United States Patent [19]

Katsumata et al.

[11] Patent Number: 4,789,492

[45] Date of Patent: Dec. 6, 1988

[54] SULFIDOXYMOLYBDENUM DIALKYLPHOSPHORODITHIOATE

[75] Inventors: Shigeru Katsumata; Takuro Handa; Tamiji Kamakura; Noriyoshi Tanaka; Hidekatsu Katoh; Kimiyoshi Namiwa; Yoshikazu Shoji, all of Tokyo, Japan

[73] Assignee: Asahi Denka Kogyo K.K., Tokyo, Japan

[21] Appl. No.: 842,333

[22] Filed: Mar. 21, 1986

[51] Int. Cl.$^4$ .................... C10M 1/48; C10M 1/38
[52] U.S. Cl. .................... 252/32.7 E; 252/42.7; 252/46.4; 252/46.7; 556/25
[58] Field of Search ............... 252/32.7 E, 42.7, 46.4, 252/46.7; 556/25

[56] References Cited

U.S. PATENT DOCUMENTS

| | | | |
|---|---|---|---|
| 3,400,140 | 9/1968 | Rowan et al. | 252/32.7 E |
| 3,446,735 | 5/1969 | Wiese | 252/32.7 E |
| 4,175,043 | 11/1979 | Horodysky | 252/32.7 E |
| 4,501,678 | 2/1985 | Katayama | 252/32.7 E |

Primary Examiner—Ferris H. Lander
Attorney, Agent, or Firm—Flynn, Thiel, Boutell & Tanis

[57] ABSTRACT

Disclosed is a novel sulfidoxymolybdenum dialkylphosphorodithioate represented by the following general formula (I):

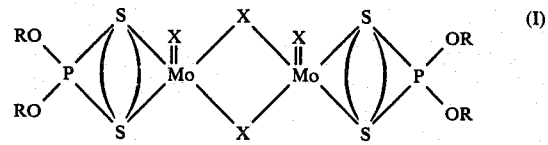

wherein R stands for a secondary alkyl group having 4 to 30 carbon atoms and four R's may be the same or different, and X stands for O or S and four X's may be the same or different.

This compound is very valuable as the lubricant additive.

20 Claims, 3 Drawing Sheets

SULFIDOXYMOLYBDENUM DIALKYLPHOSPHORODITHIOATE

BACKGROUND OF THE INVENTION (1) Field of the Invention

The present invention relates to a novel sulfidoxymolybdenum dialkylphosphorodithioate compound which is valuable as a lubricant additive.

More particularly, the present invention relates to a molybdenum-containing lubricant additive which is excellent in the antioxidant property, the antiwear property, the friction-modification property and the heat resistance and has a reduced metal-corroding property.

(2) Description of the Prior Art

It is known that various compositions are effective as lubricant additives for engine oil and the like. However, the properties required for lubricant additives become recently more severe in view of resource-saving and energy-saving effects. ZDTP has been generally used for improving the antiwear property and the like, and sulfidoxymolybdenum dialkylphosphorodithioate compounds have also been used as proposed in Japanese Patent Publication No. 8426/65 or No. 27366/69 or Japanese Patent Application Laid-Open Specification No. 110796/81.

Known sulfidoxymolybdenum dialkylphosphorodithioate compounds have a primary alkyl group or a short-chain secondary alkyl group. A sulfidoxymolybdenum dialkylphosphorodithioate compound having a primary alkyl group has a high thermal decomposition temperature and is stable, and therefore, the compound is defective in that the antiwear property is poor at low temperatures.

On the other hand, a sulfidoxymolybdenum dialkylphosphorodithioate compound having a short-chain secondary alkyl group is defective in that since the oil solubility is low, it often happens that a concentration sufficient to exert a good lubricating effect is not obtained.

Moreover, each of the foregoing known compounds has a high metal-corroding property and is not suitable for practical applications (see Information to Users, published by Caterpillar Tractor Co. on Mar. 13, 1984).

SUMMARY OF THE INVENTION

An object of the present invention is to provide a novel sulfidoxymolybdenum dialkylphosphorodithioate having a secondary alkyl group and also to provide a lubricant additive comprising this novel compound, which is excellent in the antioxidant property, the antiwear property, the friction-moderating property and the heat resistance over conventional ZDTP and molybdenum-containing lubricant additives and has a reduced metal-corroding property.

By the term "secondary alkyl group" is meant an alkyl group in which the α-position of the phosphate linkage is occupied by a secondary carbon atom.

In accordance with the present invention, there is provided a sulfidoxymolybdenum dialkylphosphorodithioate represented by the following general formula (I):

wherein R stands for a secondary alkyl group having 4 to 30 carbon atoms and four R's may be the same or different, and X stands for O or S and four X's may be the same or different.

This compound is very valuable as the lubricant additive.

DETAILED DESCRIPTION OF THE PREFERRED EMBODIMENTS

In the general formula (I), secondary alkyl groups having 4 to 10 carbon atoms are preferred as R. For example, there can be mentioned a secondary hexyl group of the following formula:

a secondary octyl group of the following formula:

a secondary heptyl group of the following formula:

a secondary pentyl group of the following formula:

a secondary butyl group of the following formula:

a secondary nonyl group of the following formula:

and a secondary decyl group of the following formula:

Secondary hexyl and secondary pentyl groups are especially preferred.

In the general formula (I), X stands for an oxygen atom or sulfur atom. It is most preferred that two of four X's, on the average, be oxygen atoms and two X's on the average be sulfur atoms. However, a satisfactory lubricating property can be obtained if the O/S ratio is from about 1/3 to about 3/1.

The compound of the general formula (I) can be obtained by reacting an aqueous solution or suspension containing (A) molybdenum trioxide or an alkali metal or ammonium molybdate and (B) an alkali metal hydrosulfide or an alkali metal sulfide represented by the general formula of $M_2S$ (in which M stands for an alkali metal or an ammonium group) at a molar ratio of from 1/0.005 to ¼ with (C) phosphorus pentasulfide and (D) a secondary alcohol [phosphorodithioic acid may be prepared in advance from (C) phosphorus pentasulfide and (D) a secondary alcohol] while adding (E) a reducing agent capable of reducing hexavalent molybdenum to pentavalent or tetravalent molybdenum in the reaction system [excluding the components (A) through (D)] in an amount of at least 1 mol per atom of molybdenum before initiation of the reaction or before completion of the reaction.

As the alkali metal molybdate used for the production of the compound of the present invention, there can be mentioned sodium molybdate, potassium molybdate and alkali metal molybdohexapolyphosphates.

As the alkali metal hydrosulfide or the alkali metal sulfide of the general formula of $M_2S$ (in which M stands for an alkali metal or an ammonium group) used as the component (B) in the present invention, there can be mentioned sodium sulfide, potassium sulfide and ammonium sulfide.

Furthermore, an aqueous solution formed by introducing hydrogen sulfide gas into an aqueous solution of a corresponding alkali metal hydroxide may be used.

It is preferred that the molar ratio of molybdenum trioxide or the alkali metal or ammonium molybdate (A) to the alkali hydrosulfide or the compound of the general formula of $M_2S$ be from 1/0.005 to ¼, and it is especially preferred that the components (A) and (B) be used in substantially equimolar amounts.

The secondary alcohol (D) used for the production of the compound of the present invention corresponds to R in the general formula (I), and compounds having an alkyl group such as those exemplified above as R and a group OH bonded to the secondary carbon atom thereof can be used as the alcohol (D).

It is preferred that phosphorodithioic acid be prepared in advance from phosphorus pentasulfide (C) and the secondary alcohol (D). Namely, both the components are reacted under reflux in substantially equimolar amounts or by using the secondary alcohol (D) in a slight excess, and if necessary, excessive secondary alcohol is removed. The excessive secondary alcohol may be used as the solvent for the reaction with molybdenum.

As the reducing agent (E) capable of reducing hexavalent molybdenum to pentavalent or tetravalent molybdenum, which is added to the reaction system before initiation of the reaction or before completion of the reaction, there can be mentioned reducing sulfur compounds such as sodium sulfoxylate, sodium dithionite, sodium sulfite, sodium hydrogensulfite, sodium pyrosulfite, sodium thiosulfate, sodium dithionate, corresponding other alkali metal and alkaline earth metal salts, hydrogen sulfide and sulfur dioxide, reducing sugars such as glucose, maltose, lactose, maltotriose and manninotriose, aldehydes such as formaldehyde, acetaldehyde and propionaldehyde, reducing acids such as formic acid, oxalic acid and ascorbic acid, and salts of these reducing acids. These reducing agents may be used singly or in the form of mixtures of two or more of them.

The compound of the present invention is valuable as a lubricant additive. The lubricant ordinarily comprises a base oil or a base chemical and additives added according to the intended use. The compound of the present invention may be used in combination with such a base oil or a base chemical and additives.

The invention also provides a lubricated composition which comprises a lubricant of the above defined sulfidoxymolybdenum dialkylphosphorodithioate in an amount to be effective for lubrication and a base oil. It is preferable that the composition comprises the lubricant in an amount of 0.001 to 1 percent by weight as molybdenum. In the practical point of view, the lubricant is contained in the composition in an amount of 0.01 to 0.02 percent by weight as molybdenum.

As the base oil or a base chemical derived from a natural oil, there can be mentioned oils, paraffinic hydrocarbons and naphthenic hydrocarbons derived from animal oils, vegetable oils and petroleum, and mixtures thereof.

As the synthetic lubricating oil, there can be mentioned hydrocarbon oils and halogen-substituted hydrocarbon oils. For example, there can be mentioned olefin homopolymers and copolymers such as polybutylene, polypropylene, a propylene/isobutylene copolymer, chlorinated polybutylene, poly(1-hexene), poly(1-octene), poly(1-decene) and mixtures thereof, alkylbenzenes such as dodecylbenzene, tetradodecylbenzene, dinonylbenzene and di(2-ethylhexyl)benzene, polyphenyls such as biphenyl, terphenyl and alkylpolyphenyls, alkyldiphenyl ethers, alkyldiphenyl sulfides, and derivatives, analogues and homologues thereof. Furthermore, there can be mentioned oils obtained by polymerization of ethylene oxide or propylene oxide, alkyl and aryl ethers thereof, and monoesters and diesters thereof with mono- or polybasic carboxylic acids. Moreover, there are included esters of various alcohols with dicarboxylic acids such as phthalic acid, succinic acid, alkylsuccinic acid, alkenylsuccinic acid, sebacic acid, adipic acid and linolic acid dimer. Valuable esters include those prepared from polyhydric alcohol ethers such as neopentyl glycol, trimethylolpropane, pentaerythritol, dipentaerythritol and tripentaerythritol. Still further, there are included silicon-containing oils such as polyalkylsiloxane oils, polyarylsiloxane oils, polyalkoxysiloxane oils, polyaryloxysiloxane oils and silicate oils, and liquid esters of phosphorus-containing acids, such as TCP, TOP and diethyl decylphosphonate.

Various additives are added according to the intended use. For example, there can be mentioned ash-forming and ash-free auxiliary detergents, dispersants, corrosion-preventing agents, antioxidants, pour point depressants, extreme pressure agents, oiliness improvers, colorants and antifoamers.

The ash-forming detergent is represented by oil-soluble neutral or basic salts such as alkali metal or alkaline earth metal salts of sulfuric acid, carboxylic acids or an organic phosphoric acid having at least one direct carbon-to-phosphorus bond, which is formed by treating an olefin polymer with a phosphorating agent such as phosphorus trichloride, phosphorus pentasulfide or a combination of phosphorus trichloride with sulfur. Sodium, potassium, lithium, calcium, magnesium, strontium and barium salts are commonly sued.

As the ash-free detergent, there can be mentioned a carboxylic acid type dispersant, an amine type dispersant, a Mannich dispersant, decyl methacrylate, vinyl decyl ether and a copolymer of an oil-soluble monomer such as an olefin having a high molecular weight with a monomer having a polar substituent such as an aminoalkyl acrylate.

Typical instances of the oiliness improver, extreme pressure agent, corrosion-preventing agent and antioxidant are as follows.

(1) Chlorinated aliphatic hydrocarbons.

(2) Organic sulfides and polysulfides, such as benzyl disulfide, bis(chlorobenzyl) disulfide, dibutyl tetrasulfide, a sulfomethyl ester of an olefinic acid, a sulfoalkylphenol, dipentene sulfide and terpene sulfide.

(3) Phosphorated and sulfurized hydrocarbons, such as a reaction product of phosphorus sulfide with terpene and a methyl ester of an olefinic acid.

(4) Phosphorus-containing esters composed mainly of dihydrocarbyl phosphites and trihydrocarbyl phosphites, such as dibutyl phosphite, diheptyl phosphite, dicyclohexyl phosphite, pentyl phenyl phosphite, dipentyl phenyl phosphite, dioctyl phosphite, tridecyl phosphite, distearyl phosphite, dimethyl naphthyl phosphite, diisobutyl substituted-phenyl phosphite, and phosphates such as tricresyl phosphate, trioctyl phosphate, tributyl phosphate, triphenyl phosphate and nonyl phenyl phosphate.

(5) Metal salts of thiocarbamic acid, such as zinc dioctyldithiocarbamate, zinc diisoamyldithiocarbamate, barium heptylphenyldithiocarbamate, antimony diisoamyldithiocarbamate, sulfidoxymolybdenum ditridecyldithiocarbamate, sulfidoxymolybdenum di-2-ethylhexyldithiocarbamate and sulfidoxymolybdenum dibutyldithiocarbamate.

(6) Phosphorodithioates of group II metals, such as zinc dicyclohexylphosphorodithioate, zinc dioctylphosphorodithioate, barium di(heptylphenyl)phosphorodithioate, cadmium dinonylphosphorodithioate and a zinc salt of phosphorodithioic acid obtained by reaction of phosphorus pentasulfide with an equimolar mixture of isopropyl alcohol and n-hexyl alcohol, and sulfidoxymolybdenum phosphorodithioate.

(7) Oiliness improvers such as oleyl alcohol, stearyl alcohol, stearic acid, isostearic acid and oleic acid.

The use of a lubricant comprising the compound of the present invention is not particularly critical. For example, the lubricant may be used as a crank case lubricating oil for a spark ignition or compression ignition internal combustion engine such as an automobile engine, a track engine, a 2-cycle engine, an air plane piston engine, a ship diesel engine or a locomotive diesel engine, a lubricating oil for a gas engine, a stationary power engine or a turbine, an automatic transmission liquid lubricant, a transmission axel lubricant, a gear lubricant, a metal-processing lubricant, a hydraulic liquid lubricant, and other lubricating oils and grease compositions.

The present invention will now be described in detail with reference to the following examples that by no means limit the scope of the invention.

EXAMPLE 1

In a nitrogen current, 1 mol of sodium molybdate was dissolved in 540 ml of water, and 1.44 mol of 40% sodium hydrosulfide was added to the solution. 0.17 mol of sodium hydrosulfite was further added. Then, 1.5 mol of di(1,3-dimethylbutyl) phosphorodithioate obtained from 4 mol of 4-methyl-2-pentanol and 1 mol of phosphorus pentasulfide was added to the mixture, and the resulting mixture was neutralized with 1.025 mol of 30% sulfuric acid. Reaction was carried out under reflux for 15 hours. The aqueous layer was removed, and the residue was purified to obtain 400 g of an oily green product. The yield was 90%.

Figure 1:
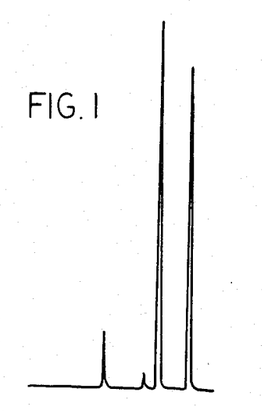
FIG. 1 is a chart of high-performance liquid chromatography of sulfidoxymolybdenum di(1,3-dimethyl butyl)phosphorodithoate prepared in Example 1.
Figure 2:
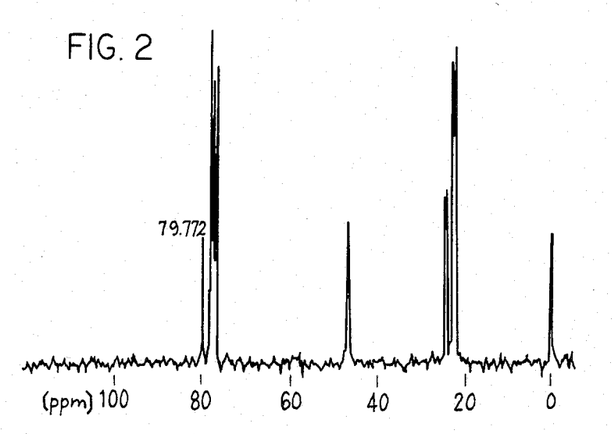
FIG. 2 is a $^{13}C$ NMR spectrum of the compound shown in FIG. 1.
Figure 3:
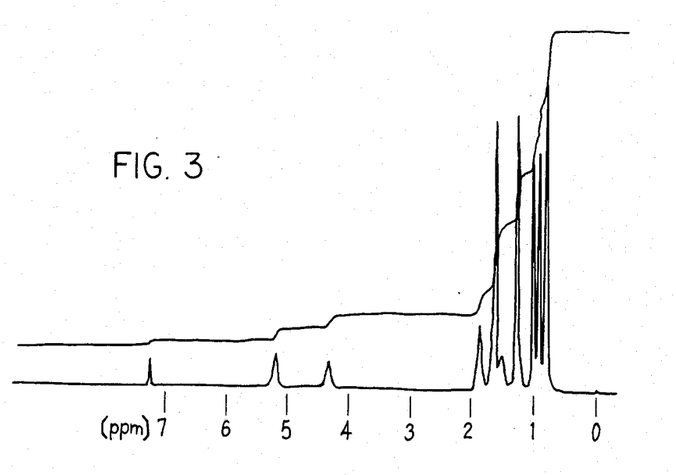
FIG. 3 is a $^{1}H$ NMR spectrum of the compound shown in FIG. 1.
Figure 4:
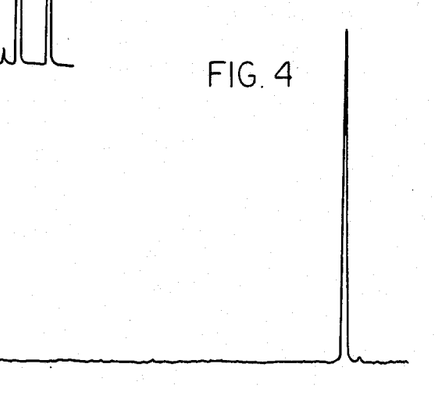
FIG. 4 is a $^{31}P$ NMR spectrum of the compound shown in FIG. 1.
Figure 5:
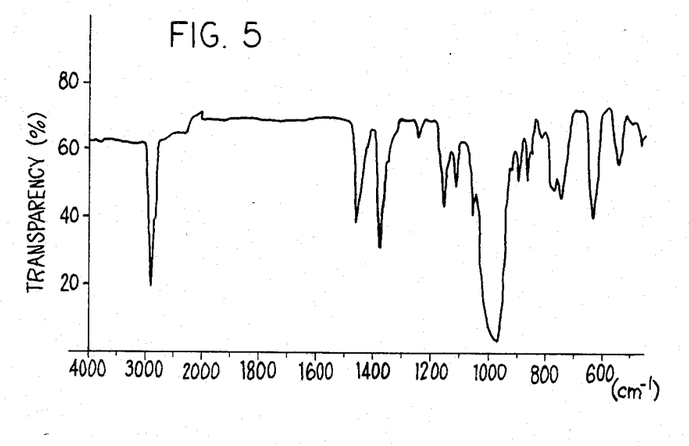
FIG. 5 is an IR spectrum of the compound shown in FIG. 1.

The elementary analysis values (the parenthesized values are calculated values) were Mo of 21.7 (21.7) % by weight, S of 22.1 (21.7) % by weight and P of 6.8 (7.0) % by weight. FIG. 1 is a chart of high-performance liquid chromatography of the product, and FIGS. 2 through 4 are $^{13}C$, $^{1}H$ and $^{31}P$ NMR spectra of the product, respectively. FIG. 5 is an infrared spectral analysis diagram of the product.

Figure 6:
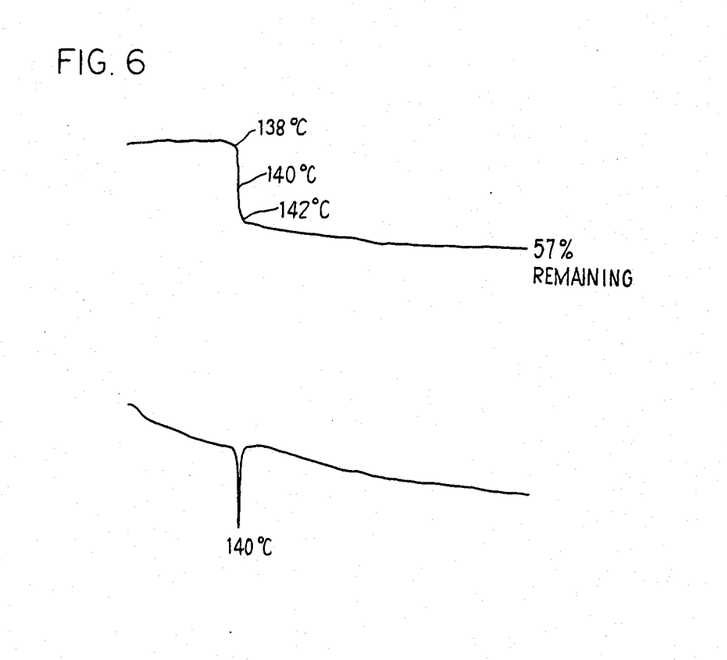
FIG. 6 is a differential thermal analysis chart of the compound shown in FIG. 1.

From the foregoing results, the product was identified as sulfidoxymolybdenum di(1,3-dimethylbutyl)-phosphorodithioate [S/O 2/2 in X of the general formula (I)]. From the results of the differential thermal analysis, it was confirmed that the thermal decomposition temperature of the product was 138° C. A chart of the differential thermal analysis of the product is shown in FIG. 6.

COMPARATIVE EXAMPLE 1

In a nitrogen current, a slurry was formed by incorporating 1 mol of molybdenum trioxide into 540 ml of water, and 1.44 mol of 40% sodium hydrosulfide was added to the slurry to dissolve molybdenum trioxide. Then, 0.17 mol of sodium hydrosulfite was added to the mixture and 1.05 mol of dihexyl phosphorodithioate obtained from 4 mol of 1-hexanol and 1 mol of phosphorus pentasulfide was further added. The mixture was neutralized with 0.525 mol of 30% sulfuric acid and reaction was carried out under reflux for 10 hours. The aqueous layer was removed, and the residue was purified to obtain 400 g an oily green product. The yield was 90%.

Figure 7:
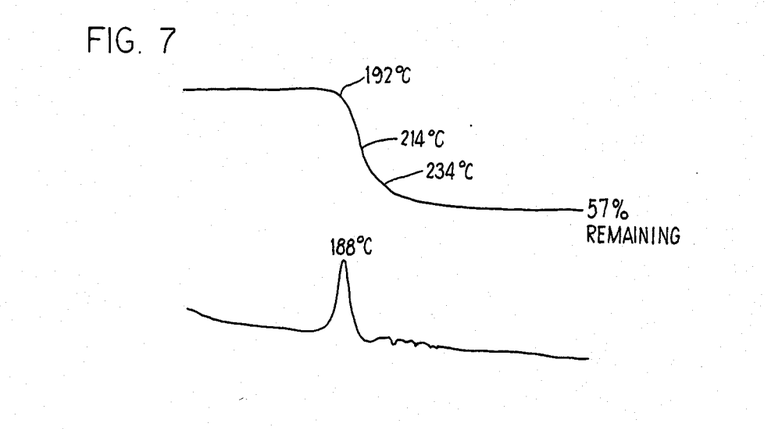
FIG. 7 is a differential thermal analysis chart of sulfidoxymolybdenum dihexylphosphorodithioate prepared in Comparative Example 1.

The elementary analysis values (the parenthesized values are calculated values) were Mo of 21.6 (21.7) % by weight, S of 22.3 (21.7) % by weight and P of 7.1 (7.0) % by weight. The product was identified as sulfidoxymolybdenum dihexylphosphorodithioate [S/O 2/2 in X of the general formula (I)]. From the results of the differential thermal analysis, it was confirmed that the thermal decomposition temperature of the product was 178° C. A chart of the differential thermal analysis of the product is shown in FIG. 7.

EXAMPLE 2

In a nitrogen current, a slurry was formed by incorporating 1 mol of molybdenum trioxide into 540 ml of water, and 1.44 mol of 40% sodium hydrosulfide was added to the slurry to dissolve molybdenum trioxide. Then, 0.17 mol of sodium hydrosulfite was added to the mixture and 1.05 mol of di(1-methylheptyl) phosphorodithioate prepared from 4 mol of 2-octanol and 1 mol of phosphorus pentasulfide was further added. The mixture was neutralized with 0.525 mol of 30% sulfuric acid and reaction was carried out under reflux for 10 hours. The aqueous layer was removed and the residue was purified to obtain 450 g of an oily green product. The yield was 90%.

The elementary analysis values (the parenthesized values are calculated values) were Mo of 19.1 (19.3) % by weight, S of 19.5 (19.3) % by weight and P of 6.3 (6.2) % by weight.

From the foregoing results, the product was identified as sulfidoxymolybdenum di(1-methylheptyl)phosphorodithioate [S/O 2/2 in X of the general formula (I)]. From the results of the differential thermal analysis, it was confirmed that the thermal decomposition temperature of the product was 142° C.

EXAMPLE 3

In a nitrogen current, a slurry was formed by incorporating 1 mol of molybdenum trioxide into 540 ml of water, and 1.44 mol of 40% sodium hydrosulfide was added to the slurry to dissolve molybdenum trioxide. Then, 0.17 mol of sodium hydrosulfite was added to the mixture and 1.05 mol of di(1-ethylpentyl) phosphorodithioate obtained from 5 mol of 3-heptanol and 1 mol of phosphorus pentasulfide was added to the mixture. The mixture was neutralized with 0.525 mol of 30% sulfuric acid and reaction was carried out under reflux for 10 hours. The aqueous layer was removed and the residue was purified to obtain 420 g of an oily green product. The yield was 90%.

The elementary analysis values (the parenthesized values are calculated values) were Mo of 20.3 (20.4) % by weight, S of 20.6 (20.4) % by weight and P of 6.6 (6.6) % by weight.

From the foregoing results, the product was identified as sulfidoxymolybdenum di(1-ethylpentyl) phosphorodithioate [S/O 2/2 in X of the general formula (I)]. From the results of the differential thermal analysis, it was confirmed that the thermal decomposition temperature of the product was 139° C.

EXAMPLE 4

In a nitrogen current, 1 mol of sodium molybdate was dissolved in 540 ml of water, and 1.44 mol of 40% sodium hydrosulfide was added to the solution. 0.17 mol of sodium hydrosulfite was further added. Then, 1.05 mol of di(1-ethylpropyl) phosphorodithioate prepared from 4 mol of 3-pentanol and 1 mol of phosphorus pentasulfide was added to the mixture, and the mixture was neutralized with 1.025 mol of 30% sulfuric acid. Reaction was carried out under reflux for 15 hours and the aqueous layer was removed. The residue was. purified to obtain 370 g of an oily green product. The yield was 90%.

The elementary analysis values (the parenthesized values are calculated values) were Mo of 23.2 (23.2) % by weight, S of 23.4 (23.2) % by weight and P of 7.6 (7.5) % by weight.

From the foregoing results, the product was identified as sulfidoxymolybdenum di(1-ethylpropyl) phosphorodithioate [S/O 2/2 in X of the general formula (I)]. From the results of the differential thermal analysis, it was confirmed that the thermal decomposition temperature of the product was 128° C.

COMPARATIVE EXAMPLE 2

In a nitrogen current, 1 mol of sodium molybdate was dissolved in 540 ml of water, and 1.44 mol of 40% of sodium hydrosulfide was added to the solution. 0.17 mol of sodium hydrosulfite was further added. Then, 1.05 mol of dipentyl phosphorodithioate prepared from 4 mol of 1-pentanol and 1 mol of phosphorus pentasulfide was added to the mixture, and the mixture was neutralized with 1.025 mol of 30% sulfuric acid. Reaction was carried out under reflux for 15 hours, the aqueous layer was removed and the residue was purified to obtain 370 g of an oily green product. The yield was 90%.

The elementary analysis values (the parenthesized values are calculated values) were Mo of 22.8 (23.2) % by weight, S of 24.0 (23.2) % by weight and P of 7.3 (7.5) % by weight. The product was identified as sulfidoxymolybdenum dipentylphosphorodithioate [S/O 2/2 in X of the general formula (I)]. From the results of the differential thermal analysis, it was confirmed that the thermal decomposition temperature of the product was 170° C.

EXAMPLE 5

In a nitrogen current, 1 mol of ammonium molybdate was dissolved in 540 ml of water, and 1.44 mol of 40% sodium hydrosulfide was added to the solution. 0.17 mol of sodium hydrosulfite was further added. Then, 1.05 mol of di(1-methylpropyl) phosphorodithioate prepared from 4 mol of 2-butanol and 1 mol of phosphorus pentasulfide was added to the mixture, and the mixture was neutralized with 1.025 mol of 30% sulfuric acid. Reaction was carried out under reflux for 15 hours and the aqueous layer was removed. The residue was purified to obtain 340 g of an oily green product. The yield was 90%.

The elementary analysis values (the parenthesized values are calculated values) were 24.5 (24.9) % by weight, S of 25.5 (24.9) % by weight and P of 7.5 (8.0) by weight.

From the foregoing results, the product was identified as sulfidoxymolybdenum di(1-methylpropyl) phosphorodithioate [S/O 2/2 in X of the general formula (I)]. From the results of the differential thermal analysis, it was confirmed that the thermal decomposition temperature was 128° C.

APPLICATION EXAMPLE 1

The compounds obtained in the foregoing examples and comparative examples were independently dissolved in a 150 neutral oil so that the molybdenum content was 0.06% by weight, and the abrasion-preventing property was determined with a shell four-ball test machine (expressed by the diameter of the wear track formed by conducting the test for 1 minute at an oil temperature of 80° C. under a load of 40 kg at 1055 rpm).

The obtained results are shown below.

| Compound Used | Wear Track Diameter (mm) |
| --- | --- |
| compound obtained in Example 1 | 0.38 |
| compound obtained in Example 2 | 0.35 |
| compound obtained in Example 3 | 0.36 |
| compound obtained in Example 4 | 0.39 |
| compound obtained in Example 5 | 0.43 |
| compound obtained in Comparative Example 1 | 0.45 |
| compound obtained in Comparative Example 2 | 0.50 |
| commercially available molybdenum compound | 0.45 |
| not added | 0.63 |

APPLICATION EXAMPLE 2

The compounds obtained in the foregoing examples and comparative examples were independently incorporated into a 500 neutral oil so that the molybdenum content was 0.05% by weight, and the antiwear property was determined with a Falex test machine.

The obtained results are shown below.

| Compound Used | Load Carrying Capacity (lb) |
| --- | --- |
| compound obtained in Example 1 | 1000 |
| compound obtained in Example 2 | 1250 |
| compound obtained in Example 3 | 1000 |
| compound obtained in Example 4 | 1000 |
| compound obtained in Example 5 | 1250 |
| compound obtained in Comparative Example 1 | 750 |
| compound obtained in Comparative Example 2 | 750 |
| commercially available molybdenum compound | 750 |
| not added | 500 |

APPLICATION EXAMPLE 3

The compounds obtained in the foregoing examples and comparative examples were independently incorporated in a 150 neutral oil so that the molybdenum content was 0.04% by weight. The abrasion-preventing property and friction-moderating property (effect of preventing elevation of the oil temperature) were determined by a Shell Four-Ball Lubricant Tester. At the start of the test, the oil temperature was 80° C., and the wear scar diameter and oil temperature were measured when the test was carried out under a load of 32 kg at 1800 rpm for 30 minutes.

The obtained results are shown below.

| Compound Used | Wear Scar Diameter (mm) | Oil Temperature (°C.) |
| --- | --- | --- |
| compound obtained in Example 1 | 0.40 | 93.0 |
| compound obtained in Example 2 | 0.38 | 92.0 |
| compound obtained in Example 3 | 0.37 | 92.6 |
| compound obtained in Example 4 | 0.40 | 92.0 |
| compound obtained in Example 5 | 0.45 | 94.3 |
| compound obtained in Comparative Example 1 | 0.47 | 100.3 |
| compound obtained in Comparative Example 2 | 0.52 | 98.7 |
| commercially available molybdenum compound | 0.48 | 98.9 |
| not added | 0.70 | 120.3 |

APPLICATION EXAMPLE 4

The antioxidant properties of the compounds obtained in the foregoing examples and comparative examples were evaluated by the oil deterioration test according to the Indiana Oxidation Stability Test. Test procedures:

The sample compound was dissolved in 200 ml of a 150 neutral oil so that the molybdenum content was 0.06 by weight, and air was circulated into the oil at a rat of 10 l/hour at 165.5° C. for 48 hours in the presence of copper and iron. The viscosity ratio (viscosity increase rate) of the oil and the increase of the acid value were determined.

The obtained results are shown below.

| Compound Used | Acid Value Increased (mg KOH/g) | Viscosity Ratio (40° C.) |
| --- | --- | --- |
| compound obtained in Example 1 | 0.15 | 1.02 |
| compound obtained in Example 2 | 0.22 | 1.01 |
| compound obtained in Example 3 | 0.18 | 1.02 |
| compound obtained in Example 4 | 0.20 | 1.01 |
| compound obtained in Example 5 | 0.18 | 1.01 |
| compound obtained in Comparative Example 1 | 0.47 | 1.12 |
| compound obtained in | 0.40 | 1.10 |

-continued

| Compound Used | Acid Value Increased (mg KOH/g) | Viscosity Ratio (40° C.) |
| --- | --- | --- |
| Comparative Example 2 commercially available molybdenum compound | 1.50 | 1.35 |
| not added | 6.50 | 30.00 |

APPLICATION EXAMPLE 5

The compounds obtained in the foregoing examples and comparative examples were independently dissolved in a 150 neutral oil so that the molybdenum content was 0.06% by weight, and a copper strip was immersed in the oil. The oil was heated at 100° C. for 3 hours and the corrosion of the copper strip was tested (according to ASTM D-130).

The obtained results are shown below.

| Compound Used | Degree of Discoloration of Copper Plate |
| --- | --- |
| compound obtained in Example 1 | 3a |
| compound obtained in Example 2 | 3a |
| compound obtained in Example 3 | 3a |
| compound obtained in Example 4 | 2e |
| compound obtained in Example 5 | 2d |
| compound obtained in Comparative Example 1 | 3b |
| compound obtained in Comparative Example 2 | 3b |
| commercially available molybdenum | 4b |

As is apparent from the foregoing description, the novel sulfidoxymolybdenum dialkylphosphorodithioate having secondary alkyl groups, provided according to the present invention, is a valuable lubricant additive which is excellent in the antioxidant property, the friction-moderating property and the heat resistance over conventional ZDTP and molybdenum-containing lubricant additives.

We claim:

1. A lubrication composition which comprises a base oil and a sulfidoxymolybdenum dialkylphosphorodithioate represented by the following general formula (I):

$$\text{RO}\diagdown_{\text{P}}\diagup^{\text{S}}\diagdown_{\text{X}}\diagup^{\text{X}}_{\text{Mo}}\diagdown_{\text{X}}\diagup^{\text{X}}_{\text{Mo}}\diagdown^{\text{S}}\diagup_{\text{P}}\diagup^{\text{OR}}_{\text{OR}} \quad (I)$$

wherein R stands for a seoondary alkyl group having 4 to 30 carbon atoms and the four R's may be the same or different, and X stands for O or S and the four X's may be the same or different.

2. A lubrication composition as set forth in claim 1, wherein R stands for a secondary hexyl group.

3. A lubrication composition as set forth in claim 1, wherein R stands for a secondary octyl group.

4. A lubrication composition as set forth in claim 1, wherein R stands for a secondary heptyl group.

5. A lubrication composition as set forth in claim 1, wherein R stands for a secondary pentyl group.

6. A lubrication composition as set forth in claim 1, wherein R stands for a secondary butyl group.

7. A lubrication composition as set forth in claim 1, wherein R stands for a secondary nonyl group.

8. A lubrication composition as set forth in claim 1, wherein R stands for a secondary decyl group.

9. A composition as claimed in claim 1, which contains from 0.001 to 1 percent by weight, calculated as molybdenum, of said sulfidoxymolybdenum dialkylphosphorodithioate.

10. A lubrication composition as set forth in claim 1 in which the four X's provide from 1 to 3 sulfur atoms and from 1 to 3 oxygen atoms.

11. A lubrication composition as set forth in claim 1 in which the four X's provide 2 sulfur atoms and 2 oxygen atoms.

12. A lubrication composition as set forth in claim 1 in which R is selected from the group consisting of $$H_3C-\underset{|}{\overset{CH_3}{CH}}-CH_2-\underset{}{\overset{CH_3}{CH}}-,\ H_3C-CH_2-CH_2-\underset{\underset{CH_3}{\overset{|}{CH_2}}}{\overset{|}{CH}}-\text{ and}$$

$$H_3C-CH_2-CH_2-CH_2-\underset{}{\overset{CH_3}{\overset{|}{CH}}}-.$$

13. A lubrication composition as set forth in claim 1 in which R is selected from the group consisting of $$H_3C-CH_2-\underset{\underset{CH_3}{\overset{|}{CH_2}}}{\overset{|}{CH}}-\text{ and }H_3C-CH_2-CH_2-\underset{}{\overset{|}{\underset{CH_3}{CH}}}-$$

14. A lubrication composition as set forth in claim 1 in which R is selected from the group consisting of $$H_3C-CH_2-CH_2-CH_2-CH_2-CH_2-\underset{}{\overset{CH_3}{\overset{|}{CH}}}-\text{ and}$$

$$H_3C-CH_2-CH_2-CH_2-CH_2-\underset{\underset{}{\overset{|}{CH_2}}}{\overset{CH_3}{\overset{|}{\phantom{C}}}}-$$

15. A lubrication compósition as set forth in claim 14 in which R is $$H_3C-CH_2-CH_2-CH_2-CH_2-CH_2-\underset{}{\overset{CH_3}{\overset{|}{CH}}}-.$$

16. A lubrication composition as set forth in claim 1 in which R is selected from the group consisting of $$H_3C-CH_2-CH_2-CH_2-\underset{\underset{CH_3}{\overset{|}{CH_2}}}{\overset{CH_3}{\overset{|}{\phantom{C}}}}-\text{ and }H_3C-CH_2-CH_2-\underset{\underset{CH_2}{\overset{|}{CH_2}}}{\overset{CH_3}{\overset{|}{\phantom{C}}}}-$$

17. A lubrication composition as set forth in claim 16 in which R is

18. A lubrication composition as set forth in claim 1 in which R is

19. A lubrication composition as set forth in claim 1 in which R is

20. A lubrication composition as set forth in claim 1 in which R is

* * * * *